US008483792B2

(12) United States Patent
Slomski et al.

(10) Patent No.: US 8,483,792 B2
(45) Date of Patent: Jul. 9, 2013

(54) ANALYTE SENSOR SUBASSEMBLY AND METHODS AND APPARATUSES FOR INSERTING AN ANALYTE SENSOR ASSOCIATED WITH SAME

(75) Inventors: Dennis Slomski, Tualatin, OR (US); Robert Bruce, Beaverton, OR (US); Jon Fortuna, Mechanicsburg, PA (US); David B. Kreitlow, Aloha, OR (US)

(73) Assignee: iSense Corporation, Willsonville, OR (US)

( * ) Notice: Subject to any disclaimer, the term of this patent is extended or adjusted under 35 U.S.C. 154(b) by 549 days.

(21) Appl. No.: 12/405,985

(22) Filed: Mar. 17, 2009

(65) Prior Publication Data

US 2009/0234212 A1 Sep. 17, 2009

Related U.S. Application Data

(60) Provisional application No. 61/037,246, filed on Mar. 17, 2008.

(51) Int. Cl.
*A61B 5/05* (2006.01)

(52) U.S. Cl.
USPC ........... 600/345; 600/309; 600/346; 600/302; 600/308; 600/371; 600/481; 600/507; 600/529; 600/545; 600/347; 606/129

(58) Field of Classification Search
USPC ............... 600/302–308, 345–371, 481–507, 600/529–545; 606/129
See application file for complete search history.

(56) References Cited

U.S. PATENT DOCUMENTS

| 4,334,541 A | * | 6/1982 | Leist et al. ............... 600/358 |
| 4,338,174 A | * | 7/1982 | Tamura ..................... 204/408 |
| 5,109,849 A | * | 5/1992 | Goodman et al. .......... 600/483 |
| 5,165,407 A | | 11/1992 | Wilson et al. |
| 5,299,571 A | * | 4/1994 | Mastrototaro .............. 600/347 |
| 5,390,671 A | * | 2/1995 | Lord et al. ................ 600/347 |
| 5,391,250 A | * | 2/1995 | Cheney et al. ............. 156/268 |
| 5,482,473 A | * | 1/1996 | Lord et al. ................... 439/67 |
| 5,568,806 A | * | 10/1996 | Cheney et al. ............. 600/373 |
| 5,586,553 A | * | 12/1996 | Halili et al. ............... 600/316 |
| 5,842,983 A | * | 12/1998 | Abel et al. ............... 204/403.1 |
| 5,931,814 A | | 8/1999 | Alex et al. |
| 5,954,643 A | | 9/1999 | VanAntwerp et al. |
| 5,965,380 A | | 10/1999 | Heller et al. |
| 6,093,172 A | * | 7/2000 | Funderburk et al. ....... 604/135 |
| 6,501,976 B1 | | 12/2002 | Sohrab |

(Continued)

FOREIGN PATENT DOCUMENTS

| FR | 2744804 | 8/1997 |
| JP | 2001-276021 A1 | 10/2001 |
| WO | WO 2007/053832 | 5/2007 |

*Primary Examiner* — Christine D Hopkins
*Assistant Examiner* — Sunita Reddy
(74) *Attorney, Agent, or Firm* — Schwabe, Williamson & Wyatt P.C.

(57) ABSTRACT

Embodiments herein provide an analyte sensor subassembly that provides an integrated structure enabling suitably secure electrical contact between an analyte sensor and the electronic components of an analyte sensor assembly. An analyte sensor subassembly assists the process of inserting the sensor into skin. An analyte sensor subassembly may operate in concert with one or more sensor insertion tools to provide insertion of an analyte sensor into the skin of a subject/patient. Associated devices, such as channel guides and sensor insertion tools, are also provided, as are methods of operation and sensor insertion.

24 Claims, 7 Drawing Sheets

U.S. PATENT DOCUMENTS

| | | |
|---|---|---|
| 6,565,509 B1 | 5/2003 | Say et al. |
| 6,671,554 B2 * | 12/2003 | Gibson et al. .................... 607/37 |
| 6,676,630 B2 | 1/2004 | Landau et al. |
| 6,695,860 B1 * | 2/2004 | Ward et al. .................... 606/185 |
| 6,699,218 B2 | 3/2004 | Flaherty et al. |
| 7,003,336 B2 * | 2/2006 | Holker et al. .................. 600/316 |
| 7,120,483 B2 * | 10/2006 | Russell et al. ................. 600/345 |
| 7,467,003 B2 * | 12/2008 | Brister et al. .................. 600/347 |
| 2003/0187338 A1 * | 10/2003 | Say et al. ....................... 600/345 |
| 2003/0211619 A1 * | 11/2003 | Olson et al. ..................... 436/44 |
| 2004/0254433 A1 | 12/2004 | Bandis et al. |
| 2006/0016700 A1 * | 1/2006 | Brister et al. .............. 205/777.5 |
| 2006/0142651 A1 | 6/2006 | Brister et al. |
| 2006/0155180 A1 | 7/2006 | Brister et al. |
| 2007/0027384 A1 * | 2/2007 | Brister et al. ................. 600/365 |
| 2007/0060801 A1 * | 3/2007 | Neinast ......................... 600/300 |
| 2008/0319414 A1 | 12/2008 | Yodfat et al. |
| 2009/0062767 A1 * | 3/2009 | Van Antwerp et al. ....... 604/504 |
| 2010/0113897 A1 * | 5/2010 | Brenneman et al. .......... 600/310 |

* cited by examiner

ANALYTE SENSOR SUBASSEMBLY AND METHODS AND APPARATUSES FOR INSERTING AN ANALYTE SENSOR ASSOCIATED WITH SAME

CROSS REFERENCE TO RELATED APPLICATIONS

The present application claims priority to U.S. Provisional Patent Application No. 61/037,246, filed Mar. 17, 2008, entitled "Analyte Sensor Subassembly and Methods and Apparatuses for Inserting an Analyte Sensor Associated with Same," the disclosure of which is hereby incorporated by reference in its entirety.

TECHNICAL FIELD

Embodiments of the present disclosure relate to analyte sensing devices, and, in particular, to an analyte sensor subassembly.

BACKGROUND

Analyte sensors facilitate the sensing of certain conditions within a patient. Electrochemical sensors are commonly used, for example, to monitor blood glucose levels in the management of diabetes. In one scheme, a sensor having an anode and a cathode is inserted through the skin so that it is surrounded by interstitial fluid. A portion of the sensor exits the skin, remaining outside the body, where electrical connections to the anode and the cathode may be made. Ensuring that a suitable electrical connection is made and is maintained is a challenge of such systems. An electronic measuring device outside the body may be used to measure electrical current from the sensor for recording and display of a glucose value. These types of devices are described, for example, in U.S. Pat. No. 5,965,380 to Heller et al. and U.S. Pat. No. 5,165,407 to Ward et al.

In addition to electrochemical glucose sensors, a number of other electrochemical sensors have been developed to measure the chemistry of blood or other body fluids or materials. Electrochemical sensors generally make use of one or more electrochemical processes and electrical signals to measure a parameter. Other types of sensors include those that use optical techniques to perform a measurement.

Although some of these devices are slender and flexible thus increasing patient comfort, such devices are difficult to insert through the skin. Unlike a typical hypodermic needle, such devices are too fragile and flexible to be simply pushed through the skin surface using normal force and speed. When the tip of such a device is forced against the skin, the device may bend and buckle with much less force than would be required to achieve skin penetration.

Current art provides several approaches for insertion of such slender flexible devices through the skin. In one case, the device is placed coaxially inside a hollow tube with a sharpened end, such as a hypodermic needle or trocar. The needle is inserted through the skin with the device inside. As a second step, the needle is withdrawn, leaving the device behind, passing through the skin into the body. See, for example, U.S. Pat. No. 6,695,860 to Ward et al. The insertion process may be painful, due to the large diameter needle, and a larger opening is made in the skin than required for passing the device alone, increasing trauma and the possibility of infection.

In a variation of this approach, the functions of the device are incorporated into a thin needle which must stay inserted into the skin. The needle provides additional mechanical strength and a sharpened point to assist in piercing the skin. However, due to its larger size and rigidity, this approach also contributes to patient discomfort for the duration of the insertion. See, for example, U.S. Pat. No. 6,501,976.

In addition, the presence of a rigid needle places mechanical constraints on the size and shape of the device housing that is attached to the surface of the skin where the device exits the skin. The needle also must be treated as a biohazard "sharp" since it is capable of transmitting disease if it should accidentally puncture the skin of another individual after being used in device insertion.

BRIEF DESCRIPTION OF THE DRAWINGS

Embodiments of the present disclosure will be readily understood by the following detailed description in conjunction with the accompanying drawings. Embodiments herein are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present disclosure.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the phrases "in an embodiment," or "in embodiments," which may each refer to one or more of the same or different embodiments. Furthermore, the terms "comprising," "including," "having," and the like, as used with respect to embodiments, are synonymous.

Embodiments herein provide an analyte sensor subassembly that provides an integrated structure enabling suitably secure electrical contact between an analyte sensor and the electronic components of an analyte sensor assembly. In an embodiment, an analyte sensor subassembly assists the process of inserting the sensor into/through skin. In embodiments, an analyte sensor subassembly may operate in concert with one or more sensor insertion tools to provide insertion of an analyte sensor through the skin and into the interstitial fluid of a subject/patient.

Figure 1A:
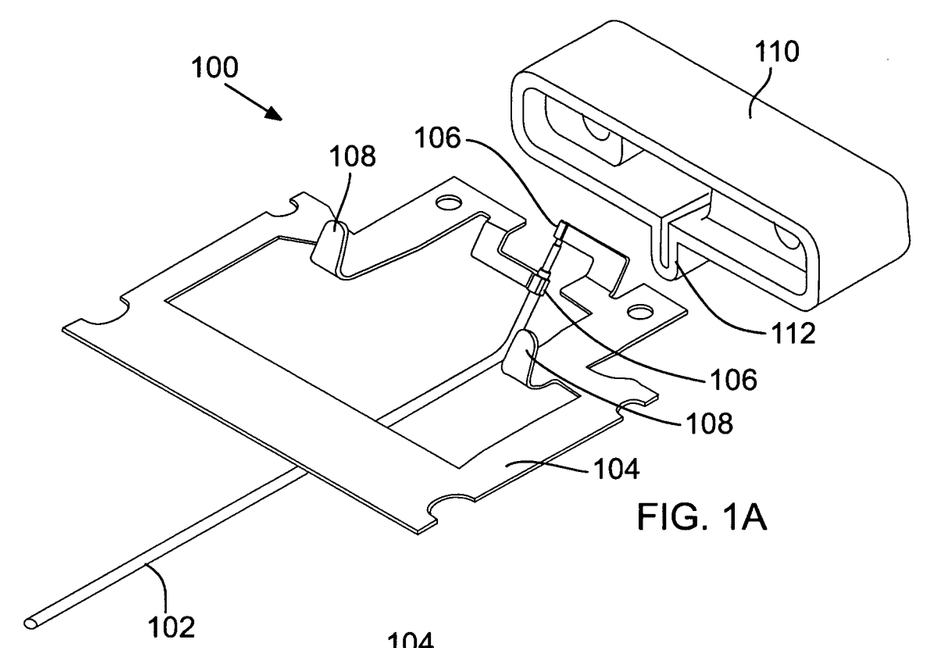
FIG. 1A shows a partially exploded view of various components of an analyte sensor subassembly in accordance with an embodiment.

FIG. 1A shows a partially exploded view of various components of an analyte sensor subassembly 100. In FIG. 1A, there is illustrated an analyte sensor 102 electrically coupled to a lead frame 104 at contacts 106, such as in the form of fingers or cups. Lead frame 104 also includes spring members 108 for providing electrical contact with a component on an analyte sensor assembly (not shown).

Subassembly 100 also includes housing 110 configured to house at least part of lead frame 104 and/or analyte sensor 102. In an embodiment, such as shown in FIG. 1A, housing 110 may be configured with a shape that corresponds to one or more components of lead frame 104 and/or analyte sensor 102 to provide a relatively secure fit of the components. Housing 110 may be configured with a shape or profile designed to mate with a channel guide assembly (not shown) to control the orientation of subassembly 100 as it moves through the channel guide assembly and/or the orientation of analyte sensor 102 as it is inserted into or through the skin. For example, housing 110 may be provided with a keel 112 that may be configured to fit within and follow a track in a channel guide assembly. Keel 112 is shown having an integrated channel to provide space for sensor 102 when subassembly 100 is assembled. The configuration of keel 112 is merely exemplary, and thus it should be appreciated that a variety of shapes and designs may be utilized to orient an analyte sensor subassembly within a channel guide assembly that would in-turn control, at least partially, the orientation and directionality of the analyte sensor during insertion. As such, housing 110 may be provided with a keel 112 or without, with multiple keel components, with other protrusions, indents, or other surface features, and/or with a non-circular cross-sectional shape/profile (square, rectangular, oval, etc.) to mate with a channel guide assembly. The non-circular cross-section of housing 110 refers to a cross-section in a plane that is transverse and perpendicular to the primary longitudinal axis of sensor 102.

Analyte sensor 102 may be any suitable sensor whether flexible or rigid. In some embodiments, a flexible sensor is one that may be flexed repeatedly, such as the type of flexion experienced by a subcutaneously implanted sensor in a human during normal movement, over a period of time (such as 3-7 days or more) without fracture. In an embodiment, a flexible sensor may be flexed hundreds or thousands of times without fracture.

Analyte sensor 102 may be substantially straight along its long axis, or one or more portions of analyte sensor 102 may be curved to provide a particular desired orientation of analyte sensor 102 in subassembly 100. As shown in FIG. 1A, a curve may be provided near the electrical contact end of sensor 102 and may be approximately 125°-135°, although other curvatures may be utilized. Housing 110 may be configured with a structure (such as keel 112) corresponding to the shape and/or orientation of analyte sensor 102, for example corresponding to the curvature of analyte sensor 102, if such a curvature is present.

Lead frame 104 may have one or more contacts 106 to electrically connect to analyte sensor 102 and one or more spring members 108 configured to electrically couple with corresponding contacts on a sensor assembly. While FIG. 1A illustrates the use of spring members 108, it should be appreciated that other electrical contact configurations may be provided without departing from the intended scope. One or more of a variety of electrical contacts may be provided on lead frame 104 to make an electrical connection with a component or electrical contact in/on a sensor assembly. Lead frame 104 may be constructed from a variety of electrically conductive materials, in whole or in part, such as a metal. Lead frame 104 may be constructed by a metal stamping and forming process in singular units or in strips or sheets comprising multiple units that may be cut during manufacture and/or assembly. In addition, while lead frame 104 is shown having a particular shape and particular supporting elements of the frame, a variety of shapes and supports may be utilized, as desired. In addition, lead frame 104 may be provided with one or more supporting structures that may enable suitable manipulation during the fabrication process and/or assembly and which may be removed during and/or after fabrication and/or assembly.

Figure 1B:
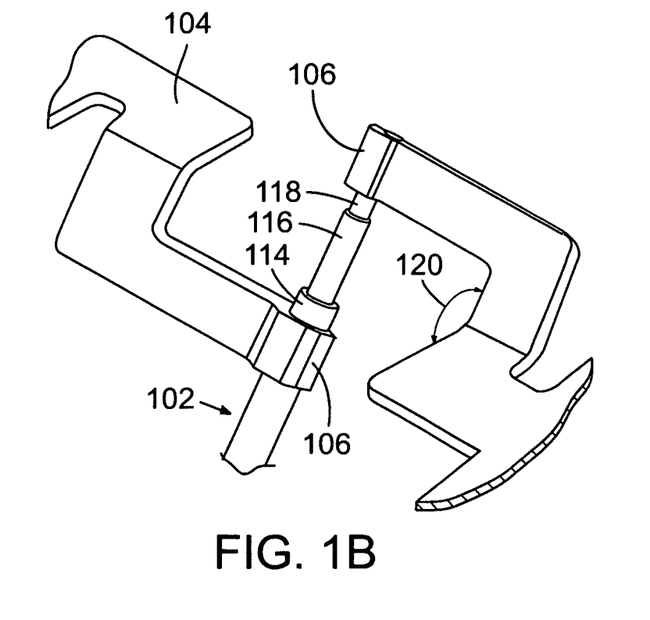
FIG. 1B shows an enhanced view of contacts and the electrical coupling of the contacts with an analyte sensor in accordance with an embodiment.

FIG. 1B shows an enhanced view of contacts 106 and the electrical coupling of contacts 106 with analyte sensor 102. Contacts 106 may be coupled to or may be part of lead frame 104 and enable an electrical signal to pass from analyte sensor 102 to lead frame 104 and, in particular to spring members 108 (or other such suitable electrical contact element(s)). In FIGS. 1A and 1B, two contacts 106 are shown; however, any suitable number of contacts may be utilized, such as 1, 2, 3, 4, or more. In FIG. 1B, contacts 106 are represented as semi-cylindrical cups, although other contact configurations may be utilized whether the same for a plurality of contacts or different for each contact.

Analyte sensor 102 may comprise multiple regions, such as electrode 114, insulation 116 (such as polyimide), and electrode 118. In an embodiment, electrode 114 may be a cathode and electrode 118 may be an anode. Contacts 106 are configured such that one contact is coupled to cathode 114 and the other contact is coupled to anode 118. Contacts 106 may be configured to engage with the size/shape of the intended contact. Each contact 106 may be configured to be electrically coupled to at least one spring member 108.

In FIG. 1B, the open sides of contacts 106 are shown in the same direction; however, if semi-cylindrical cups or other such arrangements are utilized, the cups may be oriented in different (such as opposite) directions. In embodiments, fully cylindrical or other shaped contacts may be utilized.

Contacts 106 may be bonded to electrodes 114, 118 by any suitable bonding technique, such as soldering, for example laser soldering. Laser soldering may be beneficial as a non-contact bonding method, for example, because of its minimal heat transfer, which prevents or limits damage to certain features, such as membranes present on the electrodes.

Lead frame 104 may be configured to permit manipulation during manufacture/assembly while providing suitable electrical connection of the various components. As such, analyte sensor 102 may also be provided with a curvature or directionality to separate analyte sensor 102 from at least part of lead frame 104 to make manipulating lead frame 104 easier, for example when moving the subassembly during manufacture or when removing support structures from lead frame 104. In addition, to accommodate the curvature of analyte sensor 102, if a curve is present, contacts 106 may be coupled to lead frame 104 at an angle 120 to in-turn provide proper alignment of contacts 106 with analyte sensor 102. In FIG. 1B, the angles at which each contact 106 is coupled to lead frame 104 are opposing such that the contact points of contacts 106 may be aligned with analyte sensor 102. In an embodiment, opposing angles also increase the separation distance between contacts 106 decreasing the likelihood of electrical cross-over between contacts 106. Alternatively, analyte sensor 102 may be provided with multiple curves to align with lead frame 104 and to be properly oriented for insertion into/through skin.

Figures 2A, 2B:
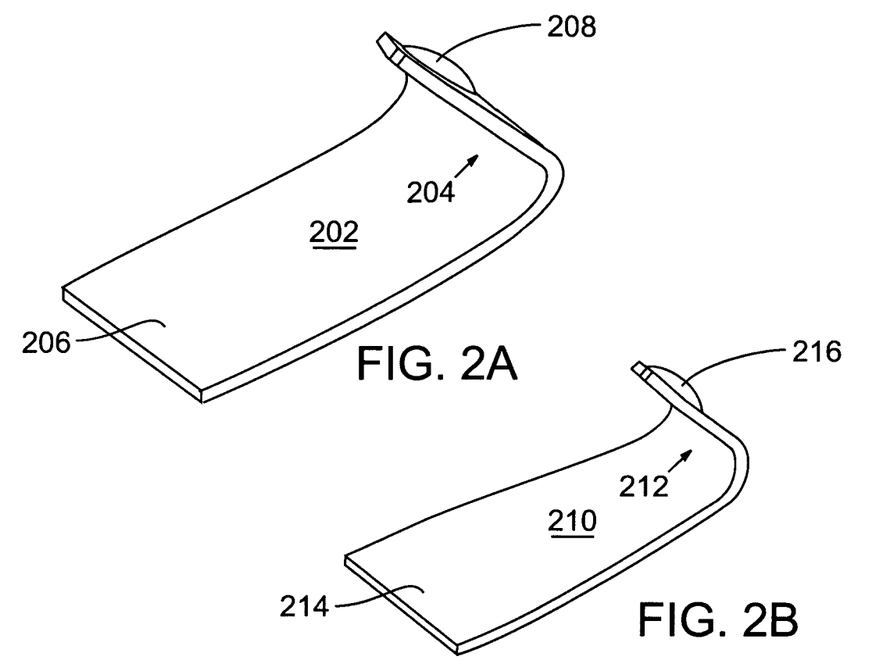
FIGS. 2A, 2B, 2C, and 2D show electrical contact spring members with a variety of shapes in accordance with embodiments herein.
Figures 2C, 2D:
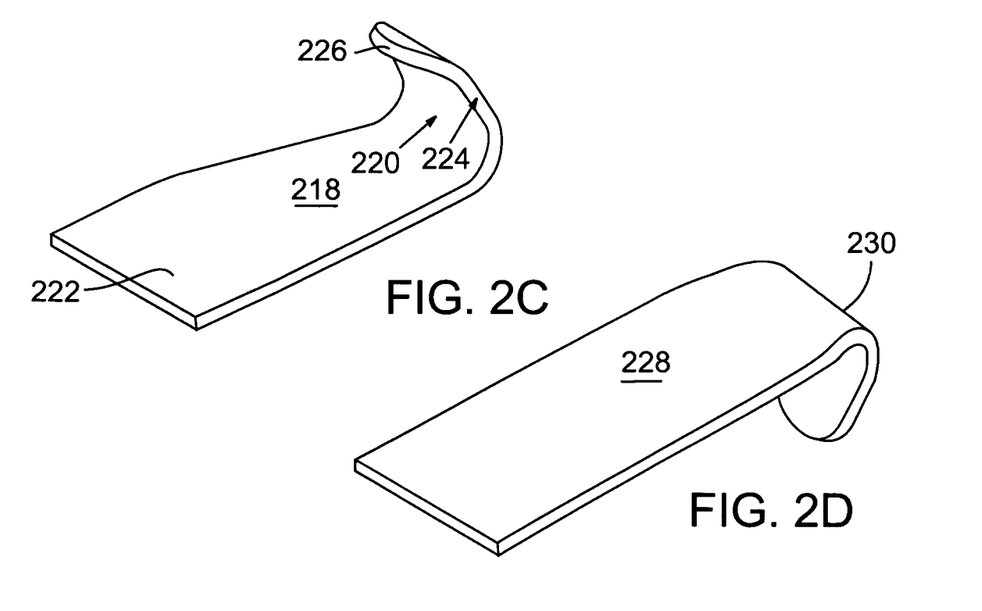

FIGS. 2A, 2B, 2C, and 2D show spring members 202, 210, 218, 228 with a variety of shapes in accordance with embodiments herein. FIG. 2A shows a spring member 202 with a contact end 204 that is wider than base 206. Contact end 204 refers to the end of spring member 202 that makes electrical contact with a corresponding component on an analyte sensor assembly (not shown). In addition, FIG. 2A shows bump 208, such as a solder bump or formed metal embossment, to serve as an electrical contact point on spring member 202. FIG. 2B illustrates a spring member 210 with a contact end 212 that is narrower than base 214 and having a bump 216. FIG. 2C illustrates a spring member 218 with a contact end 220 that is narrower than base 222 to enable tuning of the deflection and to provide a suitable contact force. In addition, spring member 218 has an extended flat region 224 providing an increased contact surface for electrical contact with a corresponding component on an analyte sensor assembly and a tip 226 curving away from a contact surface of the corresponding component (not shown). FIG. 2D illustrates a spring member 228 with a contact end 230 that is curved in a direction substantially opposite those of FIGS. 2A, 2B, and 2C. In FIGS. 2A, 2B, 2C, and 2D, the angle of curvature exhibited at the contact end may be configured as desired to enable a suitable electrical connection with a corresponding electrical contact on a corresponding component on/in the analyte sensor assembly.

In an embodiment, each spring member contact may be configured to wipe across a corresponding electrical contact. For example, each spring member contact may be configured to apply a force of approximately 80-150 grams against the corresponding contact.

As discussed above, while spring members have been shown as the electrical contact elements to electrically connect the analyte sensor to another component of the analyte sensor assembly, other suitable electrical contact elements may be utilized, including male/female type connections, pin type, brush type, etc.

Figure 3:
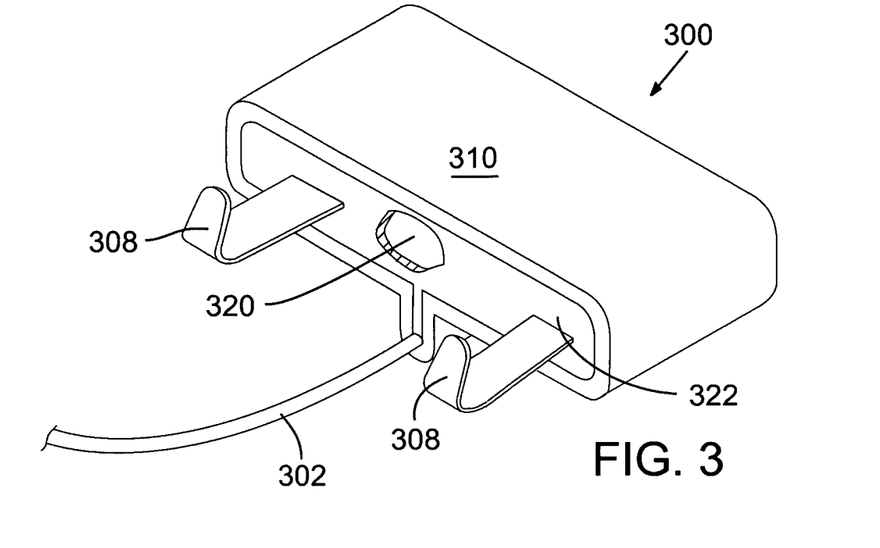
FIGS. 3 and 4 show assembled analyte sensor subassemblies in accordance with various embodiments.

FIG. 3 shows an assembled analyte sensor subassembly 300 in accordance with an embodiment. Analyte sensor subassembly 300 has an analyte sensor 302, an end of which is contained within housing 310. While not shown in FIG. 3, analyte sensor 302 may be electrically coupled to one or more portions of a lead frame (not shown) within housing 310. Regardless of whether a lead frame is utilized or which portions of the lead frame remain after assembly, contacts (not shown) or other such electrical connections may be preserved to provide an electrical connection and electrical path from analyte sensor 302 through the lead frame and to spring members 308 (or another suitable electrical contact element). During assembly of analyte sensor subassembly 300 and/or the configuration of the lead frame, if used, various portions of the lead frame may be removed. If utilized, the portions of the lead frame that may be removed may be used during one or more stages of fabrication for support and/or to enable suitable maneuverability, but may not be needed after assembly is completed.

Also shown in FIG. 3 is an encapsulant 320, such as a potting compound or packing compound, that may be used to completely or partially fill the interior cavity of housing 310 to secure the electrical connection of analyte sensor 302 and the electrical contact with, for example, certain electrical contacts. Encapsulant 320 may be provided in housing 310 in a variety of ways including introducing a flowing liquid or spreadable paste into housing 310, utilizing injection molding or other molding techniques, etc. Any suitable encapsulant may be used, such as Henkel OM 633 polyamide adhesive, which provides certain benefits due to its ability to flow at low mold pressures thereby minimizing flow induced damage to the analyte sensor and/or lead frame.

A gasket 322 may be provided to further seal housing 310. Gasket 322 may be fabricated from a polymer, plastic, rubber, etc. Gasket 322 may be inset partially in housing 310 and/or may at least partially wrap around the edges of or part of housing 310.

Figure 4:
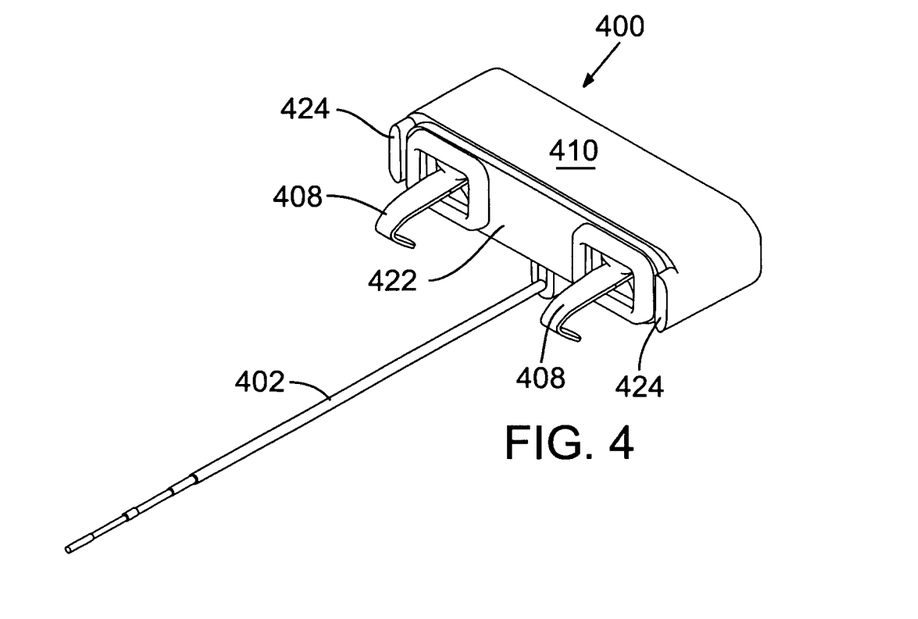

FIG. 4 illustrates an alternative assembled analyte sensor subassembly 400. Analyte sensor subassembly 400 has an analyte sensor 402, an end of which is contained within housing 410. While not shown in FIG. 4, an electrical connection between analyte sensor 402 and spring members 408 is provided within housing 410.

A gasket 422 may be provided to further seal housing 410. Gasket 422 may be fabricated from a polymer, plastic, rubber, etc. As shown in FIG. 4, gasket 422 is set between gasket stops 424 protruding from housing 410.

In embodiments, any suitable gasket may be used, for example, an injection molded Wacker 3003/20 liquid silicone resin gasket may be used.

Figure 5A:
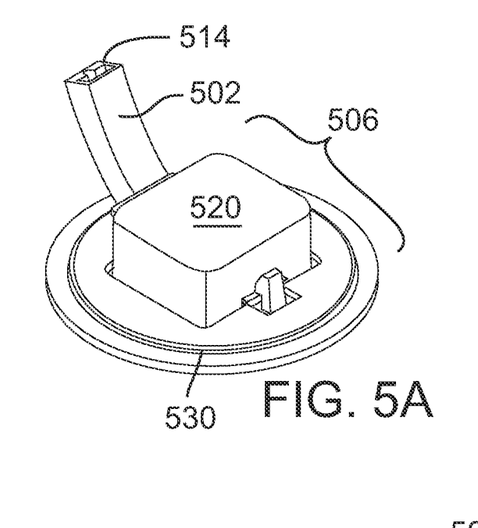
FIGS. 5A, 5B, and 5C show a channel guide assembly coupled to an analyte sensor assembly that may be used to guide the insertion of an analyte sensor subassembly into/through skin.
Figure 5B:
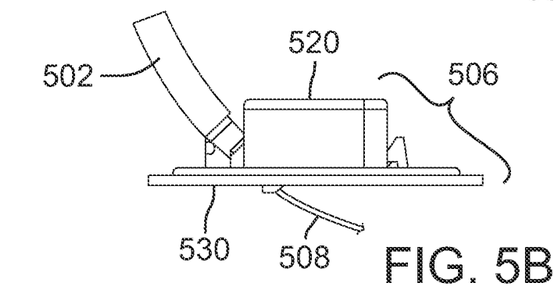
Figure 5C:
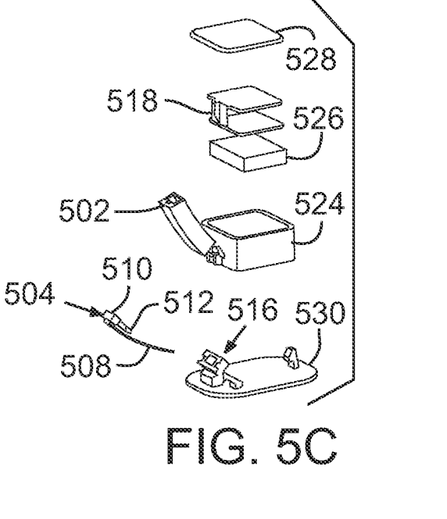

FIGS. 5A, 5B, and 5C show a channel guide assembly in cooperation with a sensor assembly. Channel guide 502 may be used to guide insertion of an analyte sensor 508 of analyte sensor subassembly 504 into/through skin and for coupling with an analyte sensor assembly 506.

Analyte sensor 508 is embodied in analyte sensor subassembly 504 to provide various electrical connections. Analyte sensor subassembly 504 also has a housing 510 and electrical contacts 512.

Analyte sensor subassembly 504 may be configured to mate with channel guide 502 for passage of analyte sensor subassembly 504 through channel guide 502. As shown, channel guide 502 may be configured to mate with analyte sensor subassembly 504 to align analyte sensor subassembly 504 for insertion of analyte sensor 508 into skin. As such, channel guide 502 may have a channel shape that corresponds to a shape of analyte sensor subassembly 504. For example, FIG. 5A illustrates a channel guide 502 with a channel 514 configured to match a correspondingly shaped analyte sensor subassembly 504. Channel guide 502 may have a non-circular cross-section that matches with a similar cross-sectional shape of analyte sensor subassembly 504. The non-circular cross-section of channel guide 502 refers to a cross-section in a plane that is transverse and perpendicular to the primary longitudinal axis of channel 514. While shown in FIGS. 5A, 5B, and 5C as curved, a suitable guidance structure may be straight or curved.

In operation, an analyte sensor subassembly 504 may be moved through channel guide 502 along channel 514 to insert analyte sensor 508 into/through skin. A mating base 516 may be provided to at least partially mate with channel guide 502. Mating base 516 may also provide a defined stop to control the depth to which analyte sensor 508 is inserted into/through skin.

Electrical contacts 512 of analyte sensor subassembly 504 may be configured for electrical connection to contacts 518. Contacts 518 may be part of a reusable sensor assembly 520. Reusable sensor assembly 520 may also comprise a housing 524, a battery 526, and a housing cover 528 that may be part of or coupled to housing 524. Reusable sensor assembly 520 may also be configured for coupling with disposable sensor assembly 530. More or less components of reusable sensor assembly 520 and/or disposable sensor assembly 530 may be provided. One or more components may be located differently than as shown in FIGS. 5A, 5B, and 5C. As such, the designations of reusable and disposable may be changed. The entire sensor assembly 506 may be reusable or disposable.

A channel guide may be integrated with an analyte sensor assembly or may be removably coupled to an analyte sensor assembly, the analyte sensor assembly comprising, for example, a reusable sensor assembly and a disposable sensor assembly. An analyte sensor of an analyte sensor subassembly may be inserted into/through skin through the channel guide such that electrical contacts on the analyte sensor subassembly may be placed into contact with electrical contacts on the reusable sensor assembly, or in an embodiment, on the disposable sensor assembly. After insertion, the channel guide may be decoupled from the sensor assembly. The sensor assembly may be used to monitor the levels of analyte in the individual, such as the individual's amount of glucose or lactate in the body.

A channel guide may be provided with an integrated sensor insertion tool, or a sensor insertion tool may be provided as a separate device that may be removably coupled to the channel guide. A sensor insertion tool provides the motive force to move the analyte sensor subassembly through the channel guide and to insert the analyte sensor into/through skin. A sensor insertion tool may provide the analyte sensor subassembly with a high speed motive force, a force sufficient to insert a flexible sensor into/through skin without requiring the initial use of a rigid introducer (i.e., a trocar, cannula, etc.).

Figure 6:
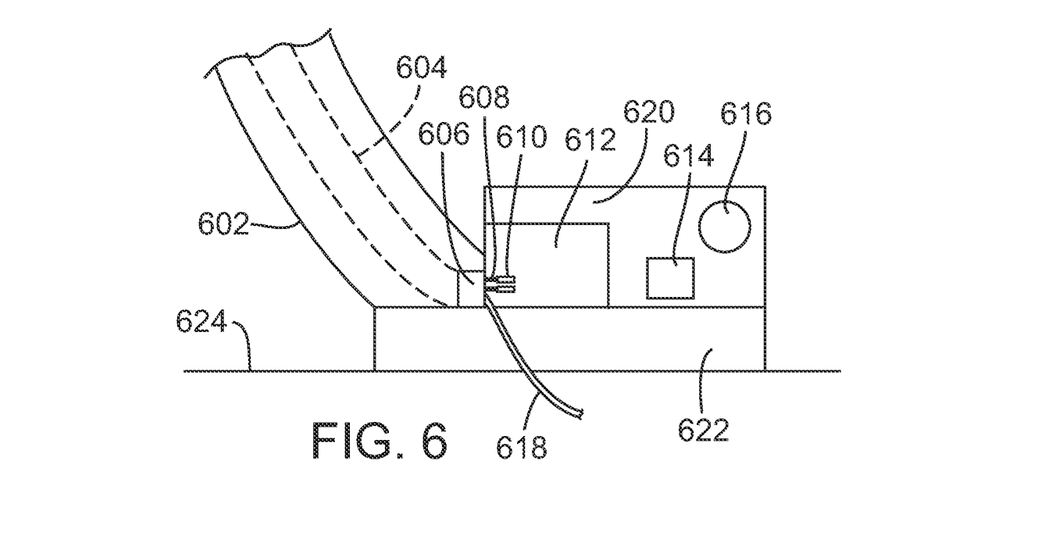
FIG. 6 shows an analyte sensor assembly in which a sensor of an analyte sensor subassembly has been inserted into/through skin and then mated with electrical contacts on a portion of the analyte sensor assembly.

FIG. 6 shows an analyte sensor assembly in which an analyte sensor 618 of an analyte sensor subassembly 606 has been inserted into skin 624. FIG. 6 shows a channel guide 602 with a channel 604. Channel 604 provides a path along which analyte sensor subassembly 606 may travel during insertion. Analyte sensor subassembly 606 has electrical contact members 608 that are configured to electrically connect with electrical contacts 610 on or electrically coupled to circuit board 612. Circuit board 612 is part of a reusable sensor assembly 620. An analyte sensor assembly may be provided as a single integrated device, or may be comprised of multiple parts, such as a reusable sensor assembly 620 and a disposable sensor assembly 622. A benefit of using a two-part sensor assembly is the ability to reuse the more expensive components, while discarding the less expensive and/or limited use components. As such, a reusable sensor assembly 620 may include various other components, such as a transmitter 614 and a battery 616.

FIGS. 7A, 7B, 7C, and 7D show various components of an analyte sensor assembly. The analyte sensor assembly comprises four primary groups of components, a reusable sensor assembly 720, a disposable sensor assembly, 730, a channel guide assembly 700, and an analyte sensor subassembly 704.

Figure 7A:
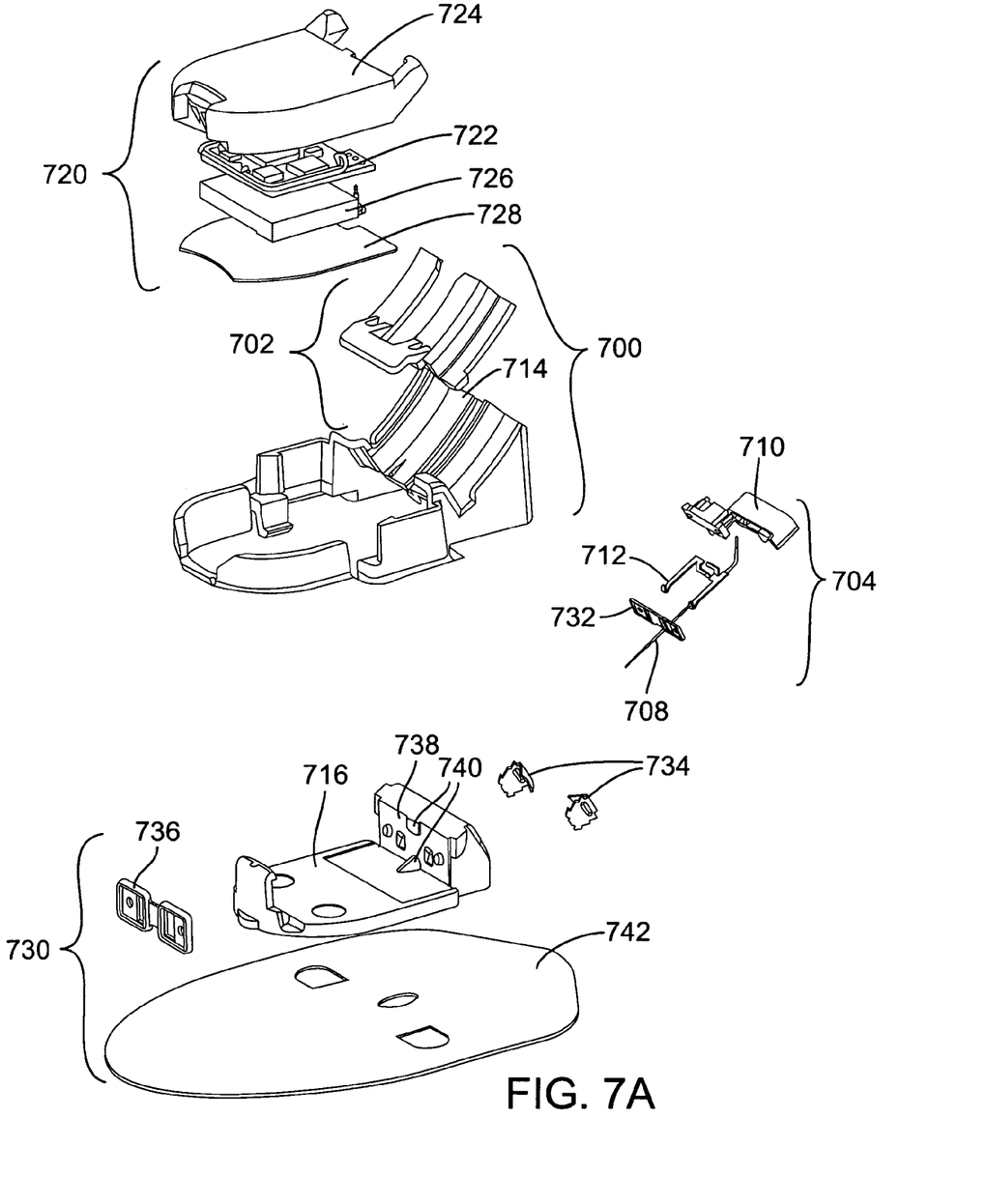
FIGS. 7A, 7B, 7C, and 7D show various components of an analyte sensor assembly in accordance with an embodiment.

FIG. 7A shows a channel guide assembly 700 configured to cooperate with a reusable sensor assembly 720 and a disposable sensor assembly 730. Channel guide 702 may be used to guide insertion of an analyte sensor 708 of analyte sensor subassembly 704 into/through skin and for electrical coupling of contacts 712 with contacts 744 (see FIG. 7D, an exploded bottom view) on reusable sensor assembly 720. Contacts 744 are in-turn electrically coupled to circuit board 722. Analyte sensor subassembly 704 thus provides electrical connection between analyte sensor 708 and reusable sensor assembly 720.

Analyte sensor subassembly 704 may be configured to mate with channel guide 702 for passage of analyte sensor subassembly 704 through channel guide 702. As shown, channel guide 702 may be configured to mate with analyte sensor subassembly 704 to align analyte sensor subassembly 704 for insertion of analyte sensor 708 into/through skin. As such, in an embodiment, channel guide 702 may have a channel shape that corresponds to a shape of analyte sensor subassembly 704. For example, FIG. 7A illustrates a channel guide 702 with a channel 714 configured to match a correspondingly shaped housing 710 of analyte sensor subassembly 704.

Figures 7B, 7C, 7D:
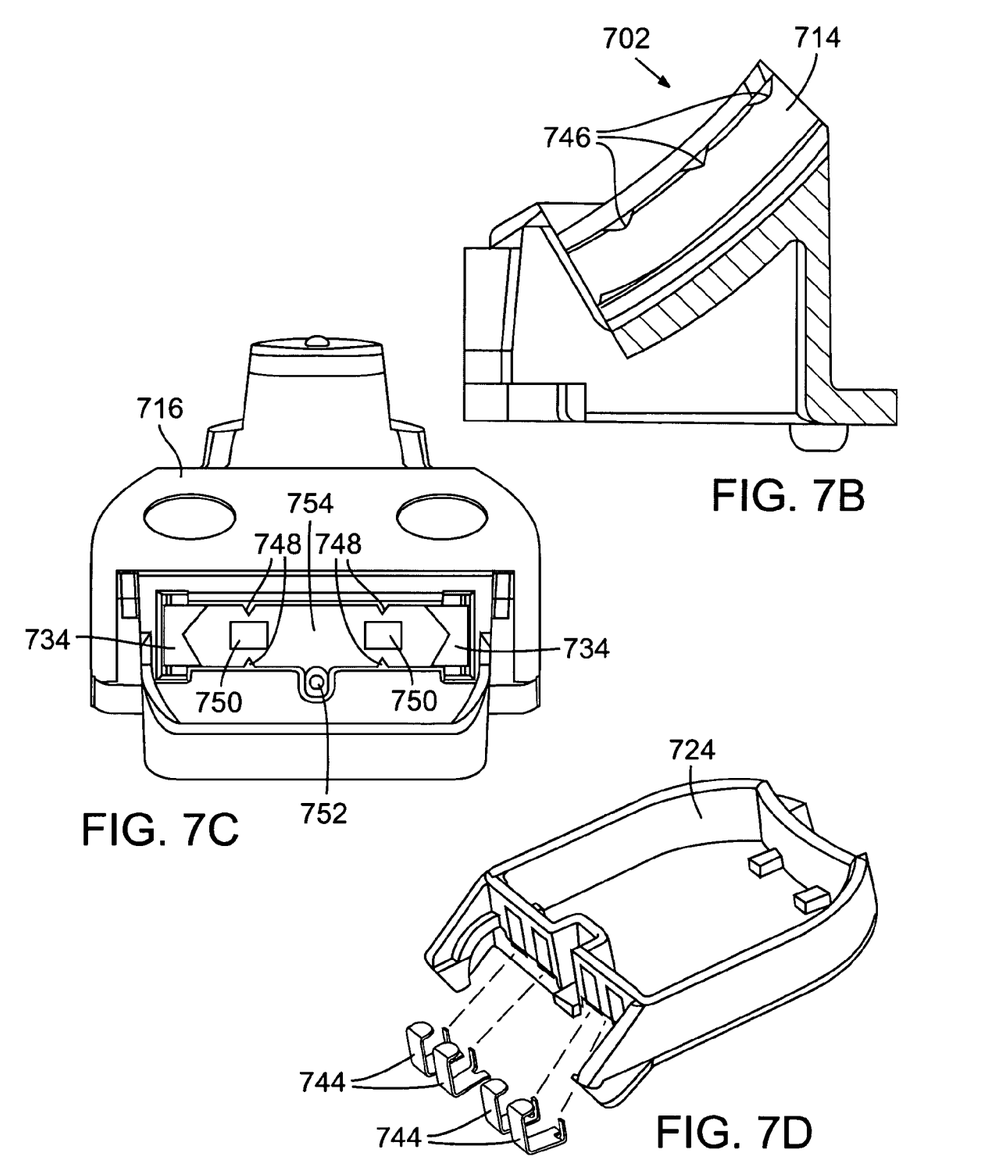

Channel guide 702 may have one or more protrusions 746 along channel 714 (see FIG. 7B, a cross-sectional side view). Protrusions 746 may retain sensor subassembly 704 in a pre-insertion position until a sufficient force is applied to sensor subassembly 704 to advance sensor assembly 704 further down channel 714. Alternatively, or in addition, protrusions 746 may aid the alignment of sensor subassembly 704 as it travels along channel 714. Protrusions 746 may be configured in matching pairs aligned along channel 714. In operation, an analyte sensor subassembly 704 may be moved through channel guide 702 along channel 714 to insert analyte sensor 708 into/through skin. After use, channel guide assembly 700 may be removed and discarded.

A housing 716 of disposable sensor assembly 730 may be provided to at least partially mate with channel guide 702. Housing 716 may also provide a defined stop to control the depth to which analyte sensor 708 is inserted into/through skin. Housing 716 also assists in aligning sensor subassembly 704 for insertion of analyte sensor 708 into/through skin, and alignment of contacts 712 with corresponding contacts on reusable sensor assembly 720.

Reusable sensor assembly 720 comprises housing 724 configured for removable coupling with disposable sensor assembly 730, circuit board 722, a battery 726, and a housing base 728 that may be part of or coupled to housing 724. More or less components of reusable sensor assembly 720 and/or disposable sensor assembly 730 may be provided.

FIG. 7C shows a rear view of housing 716 of disposable sensor assembly 730. Housing 716 includes a recess 754 in which housing 710 of analyte sensor subassembly 704 and gasket 732 reside after insertion. Gasket 732 may be provided on sensor subassembly 704 to provide a seal between sensor subassembly 704 and housing 716.

Within recess 754, retainer clips 734 are disposed. During insertion, sensor subassembly 704 contacts retainer clips 734 present in housing 716. Retainer clips 734 deflect slightly upon contact with subassembly 704 and provide a retaining (pinching) force on sensor subassembly 704. After insertion, the orientation and shape of retainer clips 734 prevents sensor subassembly 704 from backing out of its location mated with housing 716.

In addition, within recess 754, one or more ribs 748 may be provided to assist with alignment and securing of housing 710 in recess 754. Housing 716 also has a pair of openings 750 configured to permit passage of contacts 712 on sensor subassembly 704. Housing 716 also has a port 752 configured to further align sensor 708 from proper insertion into/through skin.

Associated with housing 716 of disposable sensor assembly 730, there is also a gasket 736 that seals face 738 of housing 716 against housing 724 of reusable sensor assembly 720. Face 738 may have one or more gasket stops 740 configured to properly align or orient gasket 736.

Figures 8A, 8B:
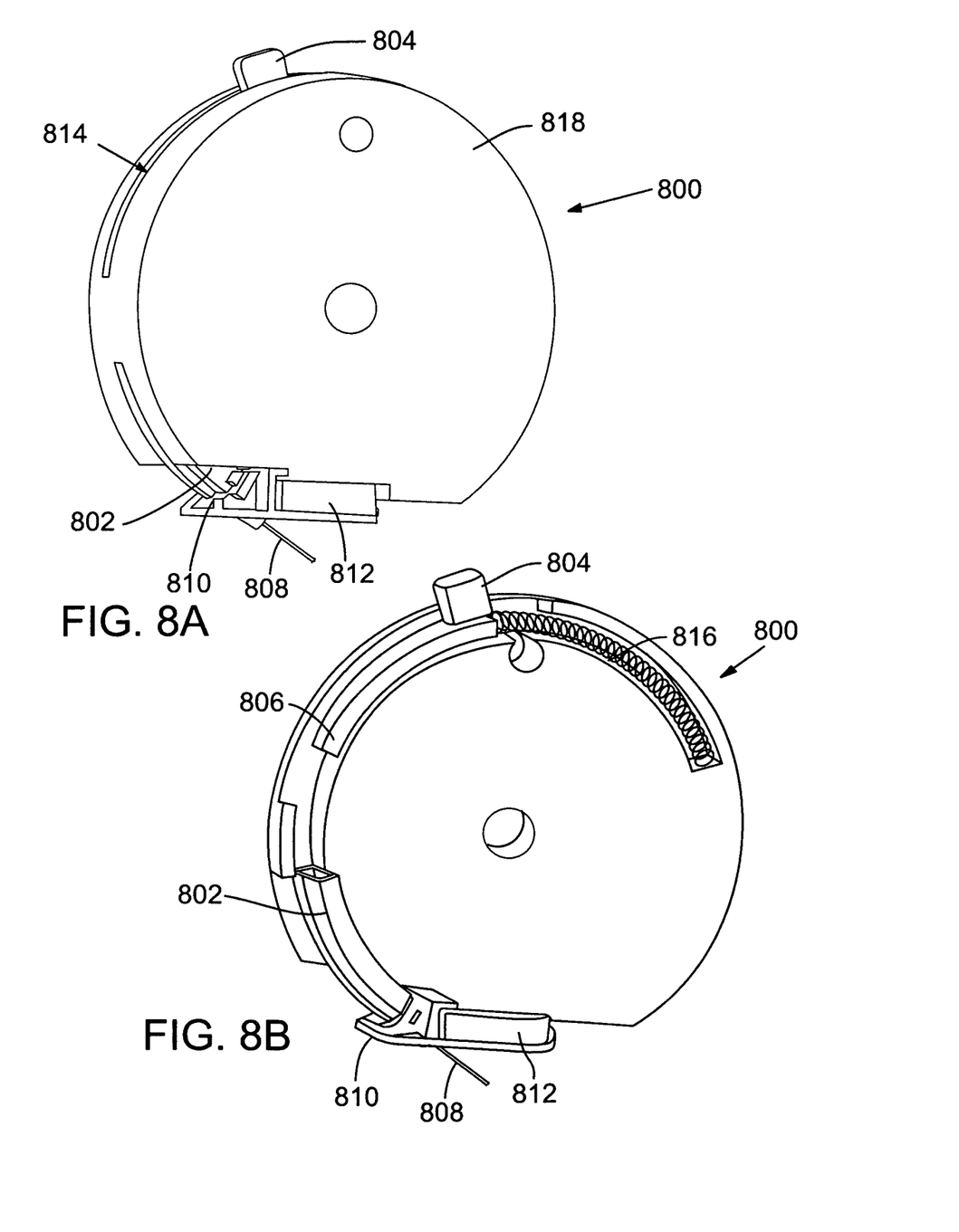
FIGS. 8A and 8B show a sensor insertion tool that may be mated to a channel guide assembly to provide a motive force to an associated analyte sensor subassembly.

As part of disposable sensor assembly 730, an adhesive patch 742 may be provided to secure the combined device to the skin of an individual. FIGS. 8A and 8B show a sensor insertion tool 800 that may be mated to a channel guide 802 to provide a motive force to an associated analyte sensor subassembly. FIGS. 8A and 8B show the coupling of sensor insertion tool 800 with disposable sensor assembly 810 and reusable sensor assembly 812. Sensor insertion tool 800 includes a cocking device 804 that may, when cocked, engage a spring, such as compression spring 816. When cocking device 804 is released, for example by actuation of a release mechanism or simply letting go of cocking device 804, spring 816 may move a plunger 806 through sensor insertion tool 900 and through channel guide 802 such that cocking device 804 travels along track 814 and plunger 806 strikes the analyte sensor subassembly to drive analyte sensor 808 into/through skin.

While FIG. 8B illustrates compression spring 816, sensor insertion tool 800 may be configured to use any suitable spring, such as a tension spring or torsion spring.

A plunger, such as provided in FIG. 8B, may have a variety of shapes and sizes. The striking end of the plunger may have a rounded end, pointed end, bullet-nose end, flat end, etc. as desired. The housing of the analyte sensor subassembly provides a surface for the plunger to strike to propel the analyte sensor subassembly through the channel guide without damaging the sensor and/or the electrical contacts in the analyte sensor subassembly.

FIGS. 8A and 8B illustrate an exemplary design of a sensor insertion tool. Other arrangements may be utilized, as desired. For example, sensor insertion tool 800 has a housing 818 that is rounded or disk-like. Other housing shapes, such as resembling a cube, a cylinder, etc. may be used. Additionally, while FIG. 8A shows a curved track 814, a straight track with a corresponding plunger may be used as an alternative.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. An analyte sensor subassembly, comprising:
    a housing;
    an analyte sensor fixed to and extending from a first side of the housing, the analyte sensor having an anode and a cathode;
    a first electrical connector having at a first end a first electrical contact coupled to the anode of the analyte sensor and at a second end a second electrical contact extending from the first side of the housing for electrical coupling to an analyte sensor assembly;
    a second electrical connector having at a first end a third electrical contact coupled to the cathode of the analyte sensor and at a second end a fourth electrical contact extending from the first side of the housing for electrical coupling to the analyte sensor assembly; and
    a striking surface on a second side of the housing, opposite the first side, for receiving a motive force to insert the analyte sensor into skin of an individual and electrically couple the second and fourth electrical contacts to the analyte sensor assembly.

2. The analyte sensor subassembly of claim 1, further comprising an encapsulant at least partially filling an interior cavity of the housing.

3. The analyte sensor subassembly of claim 2, further comprising a gasket coupled to the housing and at least partially sealing the interior cavity of the housing.

4. The analyte sensor subassembly of claim 1, wherein the housing comprises a non-circular cross-section.

5. The analyte sensor subassembly of claim 1, wherein the housing comprises a keel, wherein the keel has a channel at least partially containing the analyte sensor.

6. The analyte sensor subassembly of claim 1, wherein the analyte sensor is flexible.

7. The analyte sensor subassembly of claim 1, wherein the electrical contacts coupled to the anode and the cathode comprise semicircular cups.

8. The analyte sensor subassembly of claim 1, wherein the second and fourth electrical contacts comprise spring member contacts.

9. A sensor subassembly channel guide, comprising:
    an elongated tubular housing to mate with an analyte sensor assembly and having an interior region, an exterior surface, a first opening at a first end that is configured to receive a motive force from a motive force device to drive an analyte sensor subassembly, and a second opening at a second end that permits passage of the analyte sensor subassembly; and
    a channel located in the interior region of the housing providing a passage for the analyte sensor subassembly to pass through the sensor subassembly channel guide, said channel configured to mate with the analyte sensor subassembly.

10. The channel guide of claim 9, wherein the channel has a non-circular cross-section to align the analyte sensor subassembly.

11. The channel guide of claim 9, wherein the housing is further configured to mate with a separate motive force device.

12. The channel guide of claim 9, further comprising at least one protrusion extending from an interior surface of the channel, wherein the at least one protrusion is configured to retain the analyte sensor subassembly in a fixed position in the channel prior to application of a sufficient force.

13. The channel guide of claim 9, further comprising at least one protrusion extending from an interior surface of the channel, wherein the at least one protrusion is configured to align the analyte sensor subassembly for insertion of a sensor associated with the analyte sensor subassembly into skin of an individual.

14. A sensor insertion tool for inserting an analyte sensor into skin, comprising:
a housing having a curved track, wherein the housing mates with an analyte sensor channel guide having a curved channel;
a plunger coupled to a spring, wherein the plunger travels in or along the curved track when the spring is actuated to push an analyte sensor subassembly along a curved path within the curved channel; and
a cocking mechanism coupled to the plunger to load energy in the spring prior to inserting the analyte sensor into skin.

15. The sensor insertion tool of claim 14, further comprising a release mechanism to release the cocking mechanism and the plunger to allow the plunger to travel in or along the curved track and strike the analyte sensor or analyte sensor subassembly.

16. The sensor insertion tool of claim 14, wherein said spring is a tension or torsion spring.

17. A method of inserting an analyte sensor into skin, comprising:
providing a channel guide at least partially containing an analyte sensor subassembly, the analyte sensor subassembly having an analyte sensor and electrical contact members, the channel guide removably coupled to an analyte sensor assembly on an individual's skin and including a first opening at a first end and a second opening at a second end, the sensor assembly having electrical contacts configured to correspond to the electrical contact members of the analyte sensor subassembly;
coupling a motive force device to the channel guide; and
activating the motive force device to provide a motive force to the analyte sensor subassembly, through the first opening in the channel guide, to move the analyte sensor subassembly through the channel guide such that the analyte sensor at least partially exits the channel guide through the second opening and at least partially enters the skin, wherein the electrical contact members of the analyte sensor subassembly are thereby brought into electrical contact with the corresponding electrical contacts of the sensor assembly.

18. An analyte sensor assembly, comprising:
a first sensor assembly having a circuit board and one or more electrical contacts coupled to the circuit board;
a second sensor assembly for releasable and mechanical coupling to the first sensor assembly; and
a sensor subassembly having an analyte sensor, a housing, and one or more electrical contact members extending from the housing for electrically coupling the analyte sensor to the one or more electrical contacts on the first sensor assembly, the sensor subassembly configured to mechanically engage with the second sensor assembly during use and only after the analyte sensor has been at least partially inserted into skin of an individual.

19. The analyte sensor assembly of claim 18, further comprising a gasket coupled to the sensor subassembly to provide a seal between the sensor subassembly and the second sensor assembly after insertion of the analyte sensor.

20. The analyte sensor assembly of claim 18, further comprising a gasket coupled to the second sensor assembly to provide a seal between the first and second sensor assembly when the first and second sensor assembly are coupled together.

21. The analyte sensor assembly of claim 18, wherein the second sensor assembly further comprises a recess to engage with the sensor subassembly during and after insertion of the analyte sensor.

22. The analyte sensor assembly of claim 21, further comprising one or more retainer clips disposed in the recess to restrict retraction of the sensor subassembly from engagement with the second sensor assembly.

23. The analyte sensor assembly of claim 21, further comprising one or more ribs disposed in the recess to align the sensor subassembly during and after insertion of the analyte sensor.

24. The analyte sensor assembly of claim 18, wherein the one or more electrical contact members of the sensor subassembly are configured to electrically couple with the one or more electrical contacts of the first sensor assembly only after the analyte sensor has been at least partially inserted into the skin.

* * * * *